United States Patent [19]

Takamatsu, deceased et al.

[11] Patent Number: 4,475,540
[45] Date of Patent: Oct. 9, 1984

[54] ENDOSCOPE APPARATUS

[75] Inventors: Takeshi Takamatsu, deceased, late of Hachioji, Japan; by Tokuyuki Takamatsu, legal representative, Tokyo, Japan

[73] Assignee: Olympus Optical Co., Ltd., Tokyo, Japan

[21] Appl. No.: 437,326

[22] Filed: Oct. 28, 1982

[30] Foreign Application Priority Data

Nov. 4, 1981 [JP] Japan .................................. 56-176913

[51] Int. Cl.³ .............................................. A61B 1/06
[52] U.S. Cl. ........................................... 128/6; 358/98
[58] Field of Search ........................................ 128/4-8; 354/62; 358/98, 141, 142; 362/32

[56] References Cited

U.S. PATENT DOCUMENTS 4,281,910  8/1981  Takayama ............................... 128/4
4,349,014  9/1982  Takamatsu ............................. 128/6
4,403,605  9/1983  Tanikawa ............................... 128/6

FOREIGN PATENT DOCUMENTS 0017464  10/1980  European Pat. Off. ................. 128/6
0025958   4/1981  European Pat. Off. ................. 128/6

*Primary Examiner*—Edward M. Coven
*Assistant Examiner*—Max F. Hindenburg

[57] ABSTRACT

An endoscope apparatus is composed of an endoscope unit, a light source unit and a camera unit. The light source unit has a control station transmission circuit which becomes a control station. When the camera unit is mounted in the endoscope unit and the self address codes transmitted from the controlled station transmission circuit of the camera unit by n times are received by the control station transmission circuit of the light source unit by m times, the control station transmission circuit identifies the connection of the camera unit.

5 Claims, 6 Drawing Figures

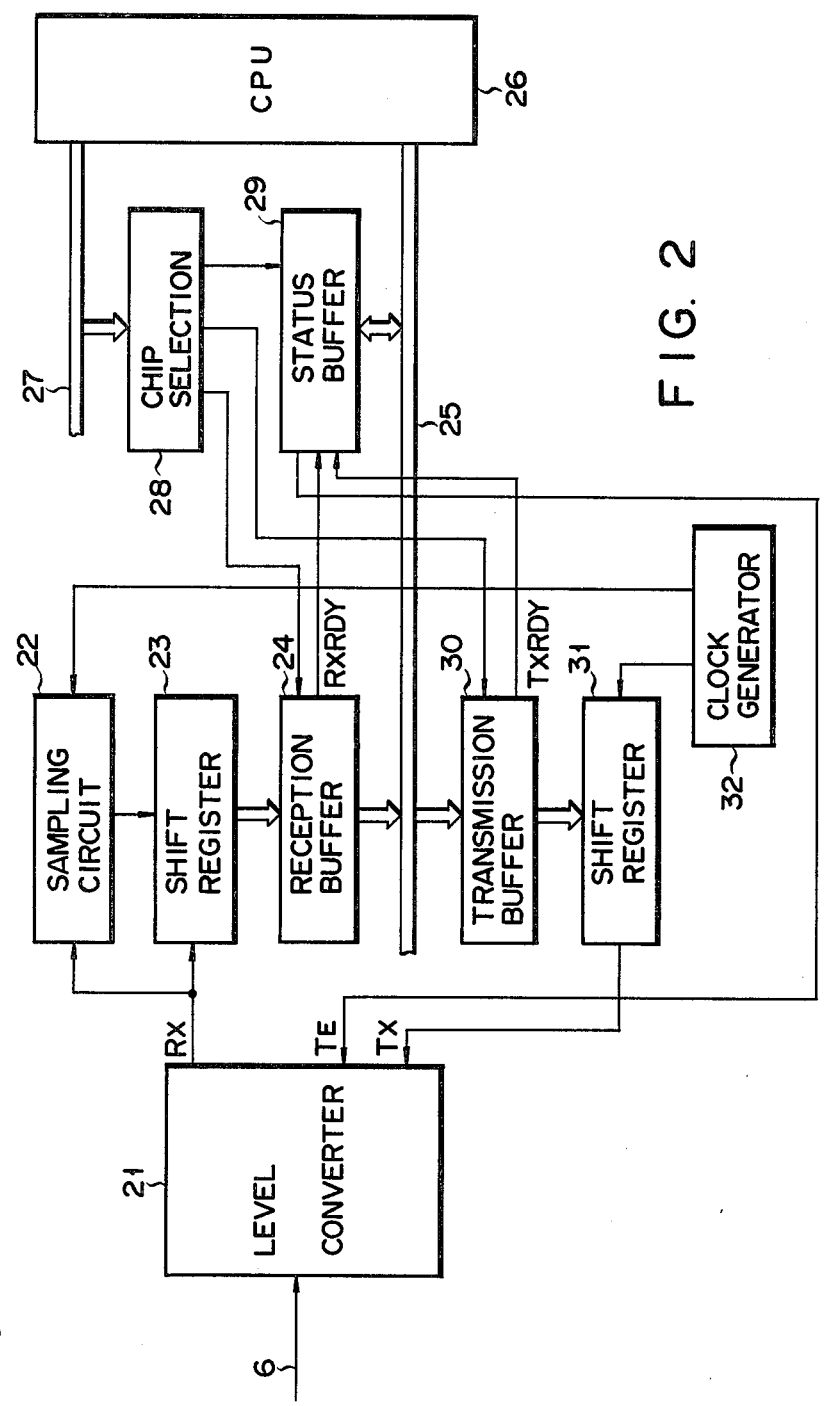
F I G. 2

ENDOSCOPE APPARATUS

BACKGROUND OF THE INVENTION

The present invention relates to an endoscope apparatus and, more particularly, to an endoscope apparatus which performs data transmission among an endoscope unit, a light source unit and a camera unit.

An endoscope apparatus which performs data transmission among an endoscope unit, a light source unit and a camera unit, thereby controlling the operation such as air feeding, water feeding, suction or a photographing has been developed. According to such an endoscope apparatus, the light source has been constructed to function as a control station, and the endoscope unit and the camera unit have been constructed to function as a controlled station. In the conventional endoscope apparatus, a light source unit requires a period of time until it starts controlling a unit by performing the check of an address of the unit. For example, when the camera is mounted on the eyepiece of the endoscope unit and the light source is controlling only the endoscope unit, the light source unit requires a period of time until it checks the address of a camera unit to identify the connection of the camera unit and then transmits an initial data to the camera unit. Accordingly, if an operator operated the camera unit before the initial data had been transmitted to the camera unit, the camera unit might operate erroneously.

SUMMARY OF THE INVENTION

It is an object of the present invention to provide an endoscope apparatus which does not operate erroneously when an endoscope unit, a light source unit and a camera unit are attached or detached.

According to the present invention, there is provided an endoscope apparatus in which, when a unit that functions as a controlled station is connected to function as a control station, the unit of the controlled station transmits a self address code to the unit of the control station for a predetermined period of time and registers the unit of the controlled station in response to the self address code.

BRIEF DESCRIPTION OF THE DRAWINGS

FIG. 2 is a circuit diagram of a transmission circuit;

DETAILED DESCRIPTION OF THE PREFERRED EMBODIMENTS

The present invention will now be described in more detail with reference to the accompanying drawings.

Figure 1:
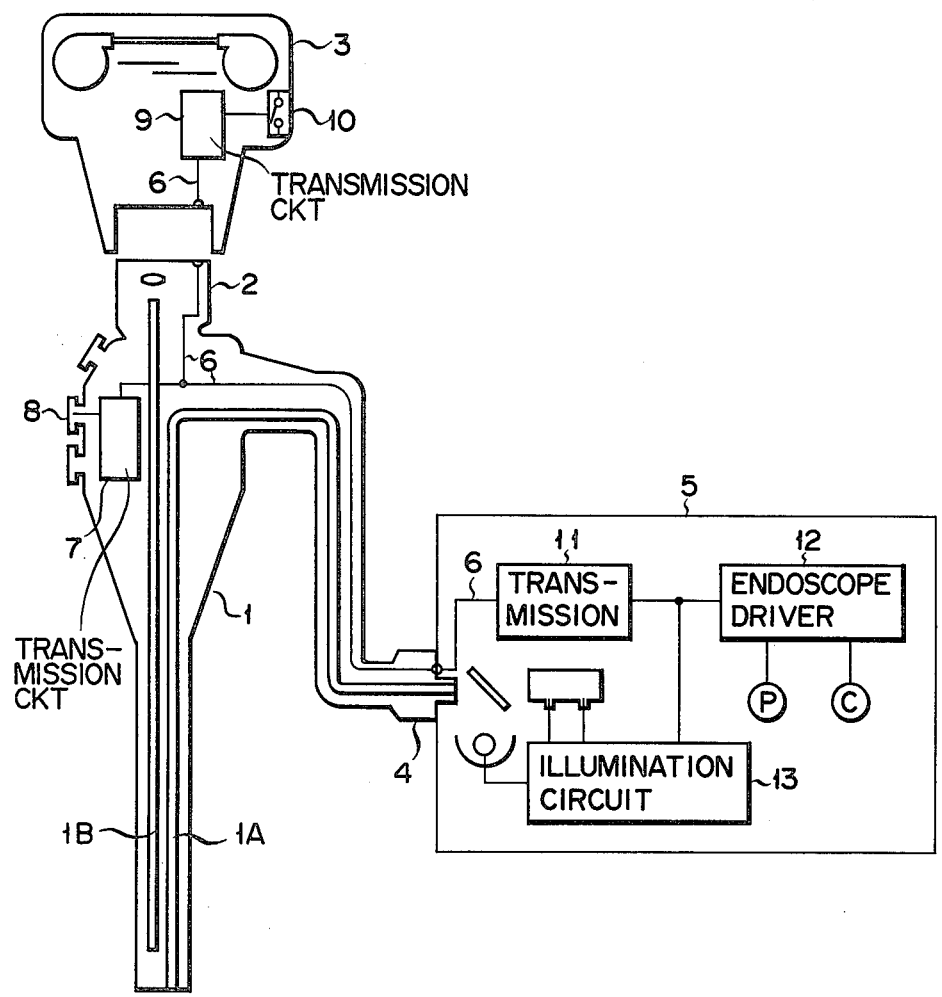
FIG. 1 is a schematic circuit diagram of an endoscope apparatus according to an embodiment of the present invention.

In FIG. 1, a camera unit 3 is mounted on the eyepiece unit 2 of an endoscope unit 1, and the connector 4 of the unit 1 is connected to a light source unit 5. A transmission circuit 7 of the unit 1 is connected, for example, to an operation switch such as an air feed switch 8 and is further connected through a transmission line 6 to the transmission circuit 9 of the camera unit 3 and to the transmission circuit 11 of the light source unit 5. The transmission circuit 11 of the unit 5 functions as a control station, and the transmission circuits 7 and 9 of the units 1 and 3 function as a controlled station. An operation switch of the camera unit 3 such as, for example, a release switch 10 is connected to the transmission circuit 9, and the transmission circuit 11 is connected to an endoscope control circuit 12 for controlling air feed, water feed, and suction, and to an illumination control circuit 13 for controlling the illumination for photographing an image.

In the endoscope unit 1 are provided a light guide 1A which is led from the connector 4 to the end of the endoscope unit, and an image guide 1B which is led from the end of the endoscope unit to the eyepiece unit 2.

In FIG. 2, the circuit configuration of the transmission circuits 7, 9 and 11 is shown. In the circuit shown in FIG. 2, there is provided a level converter circuit 21 connected to the transmission line 6. The output terminal Rx of the converter 21 is connected to a sampling circuit 22 and a shift register 23. The output terminal of the sampling circuit 22 is connected to the shift register 23. The output port of the shift register 23 is connected through a reception buffer 24 to a data bus 25. The data bus 25 is connected to a CPU 26. An bus 27 connected to the CPU 26 is connected to a chip selection circuit 28. The output terminal of the circuit 28 is connected to the reception buffer 24, a status buffer 29 and a transmission buffer 30, respectively. The input/output port of the buffer 29 is connected to the buffer 25, and the signal output terminal is connected to the level converter 21. The buffers 24 and 30 are connected to the buffer 29 for receiving an RxRDY signal and a TxRDY signal. The RxRDY signal represents the reception of the received data for characters, and the TxRDY represents the state of enabling the reception of a transmission data by the buffer 30. The output port of the buffer 30 is connected to a shift register 31. The output terminal of the shift register 31 is connected to the input terminal Tx of the converter 21. A clock generator 32 is connected to the sampling circuit 22 and the shift register 31.

Figure 3:
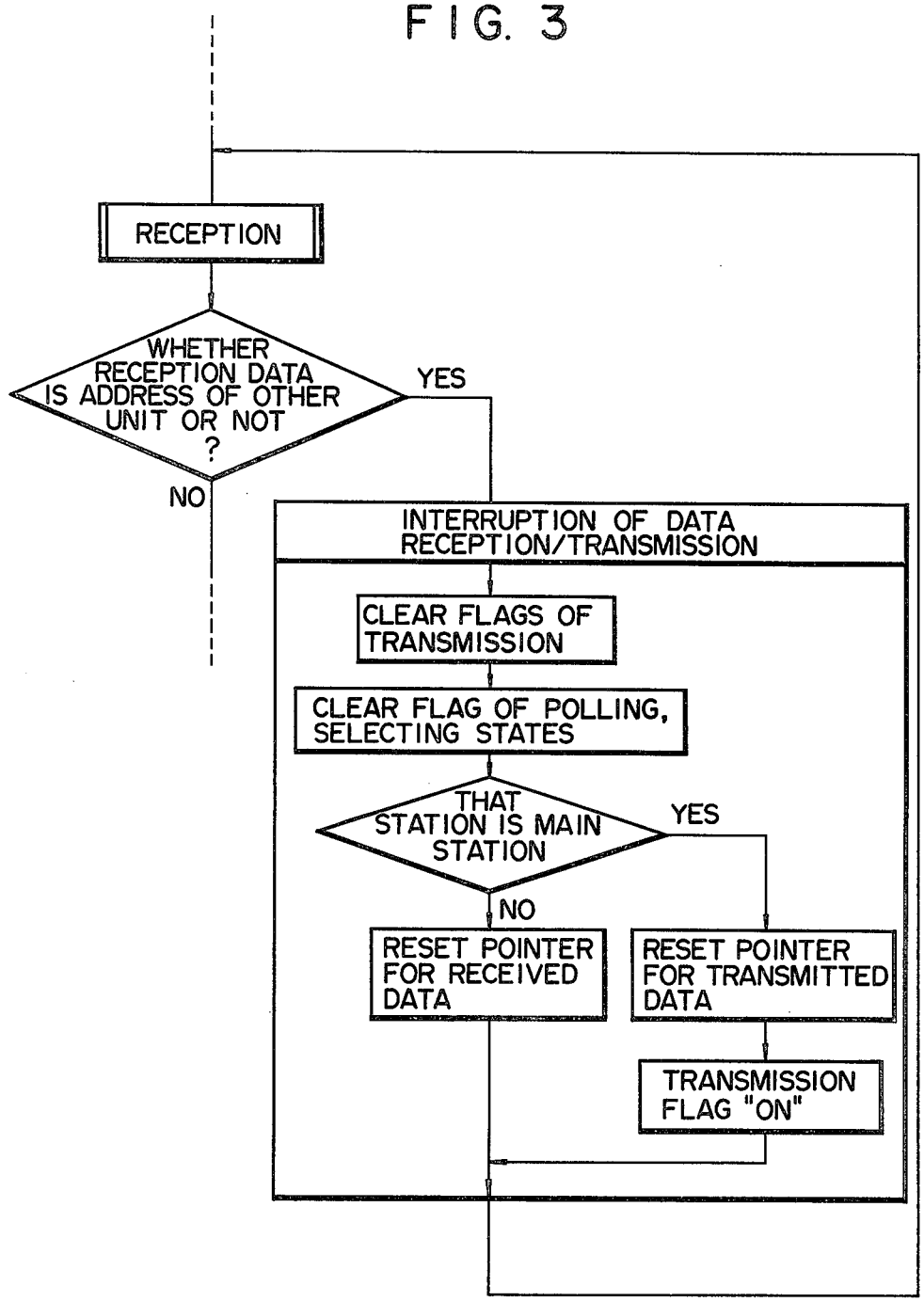
FIG. 3 is a flowchart for explaining the operation of the transmission circuit of the endoscope unit.
Figure 4:
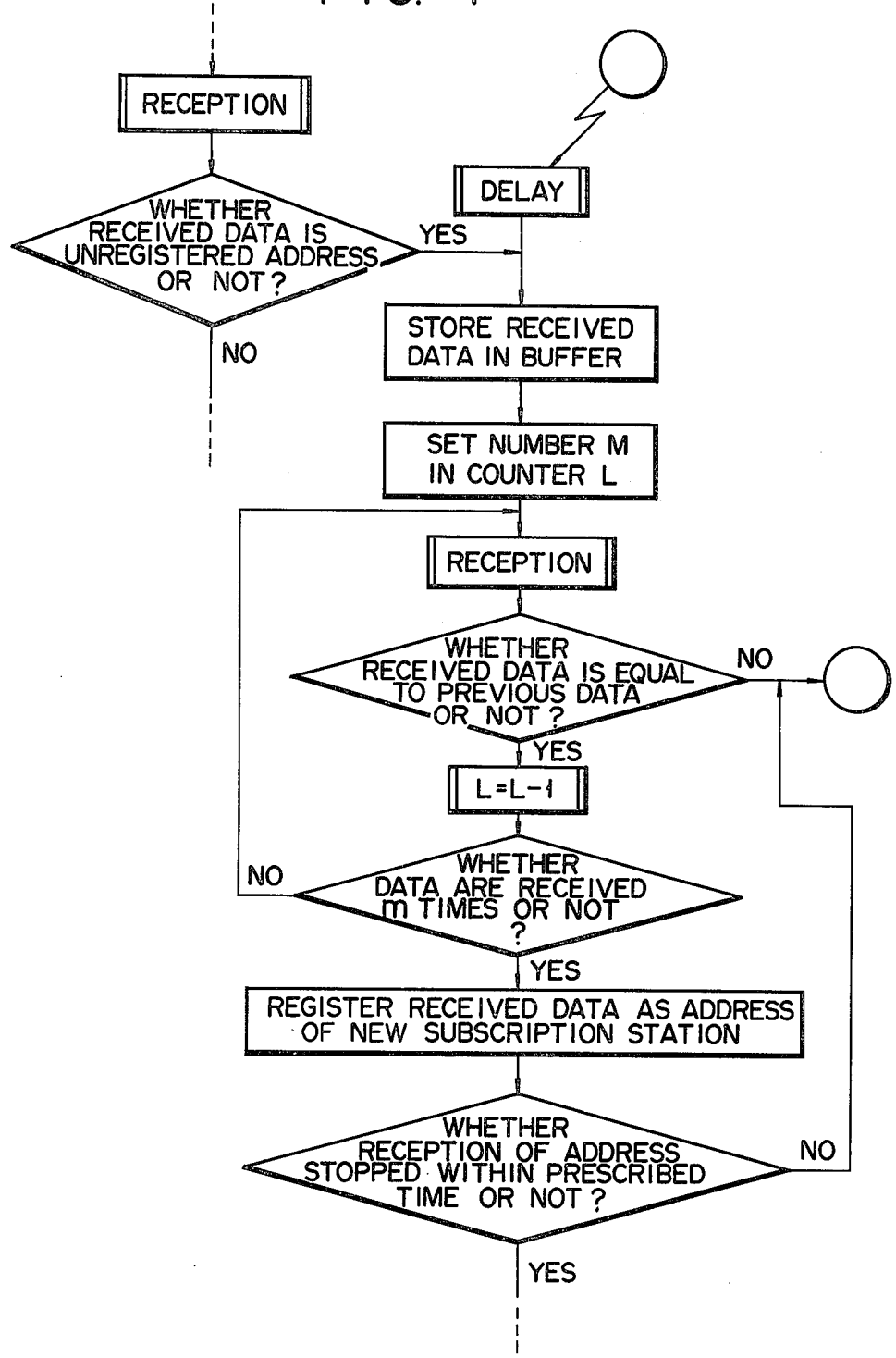
FIG. 4 is a flowchart for describing the operation of the transmission circuit of a light source unit.
Figure 5:
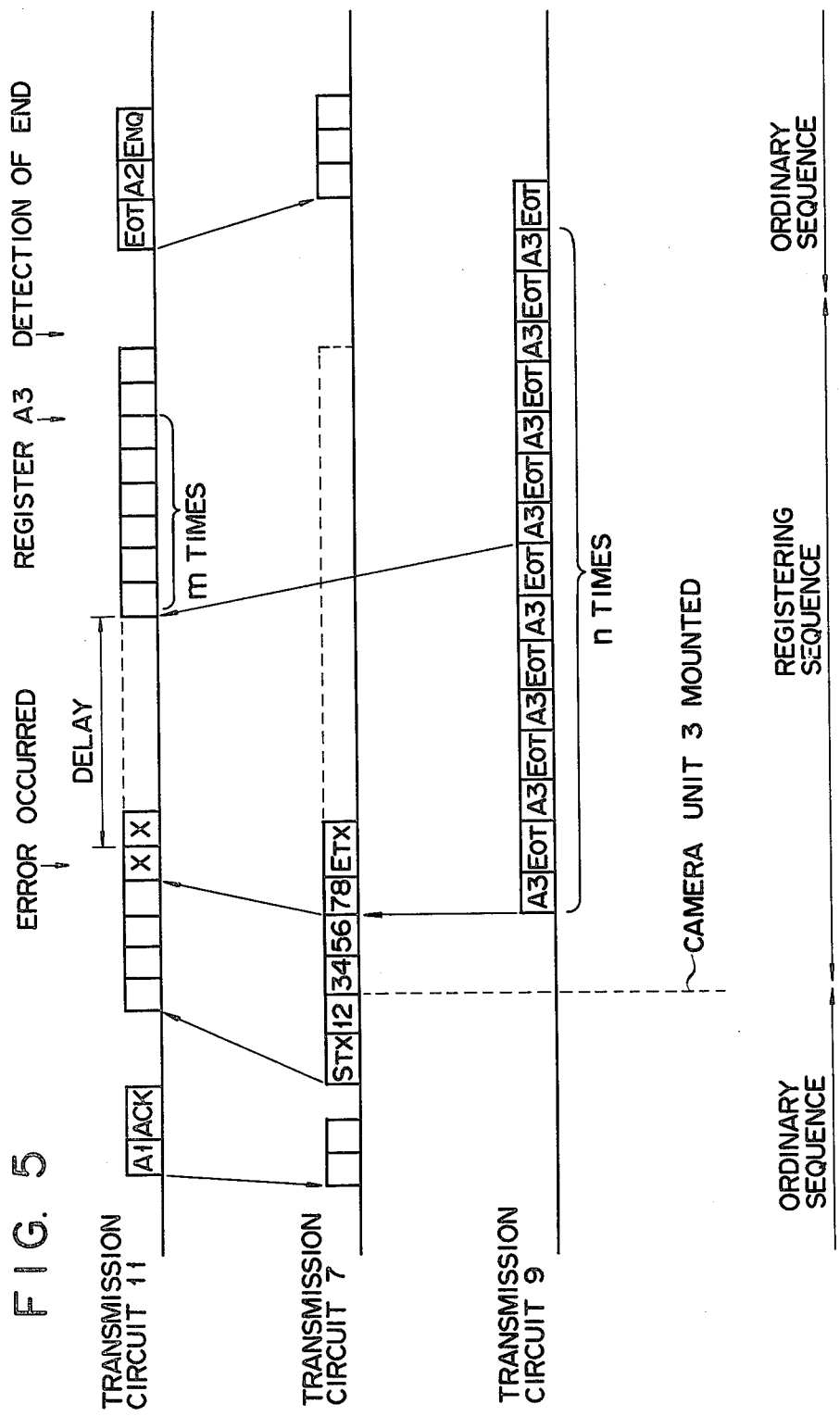
FIG. 5 is a timechart for describing the transmission of data.
Figure 6:
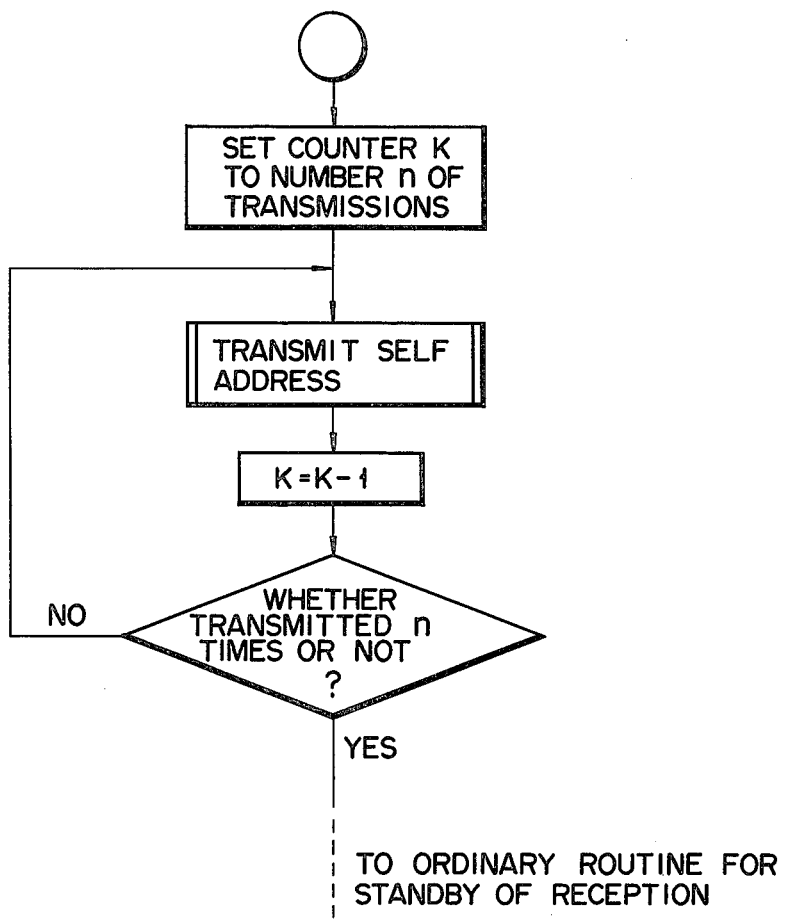
FIG. 6 is a flowchart for describing the operation of the transmission circuit of a camera unit.

The operation of the endoscope apparatus thus constructed will be described. When only the endoscope unit 1 is connected to the light source unit 5, the transmission circuit 7 of the endoscope unit and the transmission circuit 11 of the light source unit 5 communicate with each other. In this case, the CPU 26 of the transmission circuit 11 of the light source unit 5 recognizes merely the self address code A1 and the address code A2 of the transmission circuit 7 of the endoscope unit 1. At this time, the transmission circuits 7 and 11 of both the units 1 and 5 communicate data with each other which is to be ordinarily received and processed as shown in the flowcharts in FIGS. 3 and 4. In other words, as shown in the timechart in FIG. 5, the transmission circuit 11 transmits an acknowledge data A1-·ACK to the transmission circuit 7, and the transmission circuit 7 responds to the data A1·ACK and transmits a test data STX 12, . . . to the transmission circuit 11. Thus, the CPU 26 of the transmission circuit 11 delivers an endoscope operation command such as air feed, water feed, suction, etc. to the endoscope control circuit 12 in accordance with the text data. The circuit 12 drives a suction pump P or a compressor C in response to the command. When the camera unit 3 is mounted on the eyepiece unit 2 of the endoscope unit 1 and the power source of the camera unit 3 is turned on during the transmission of the test data, the camera unit 3 sets a self address code transmission number in the counter K of the transmission circuit 9 as shown in the flowchart in FIG. 6. The transmission circuit 9 transmits n times (e.g., 8 times) the self address code A3-EOT shown in FIG. 5. When the camera address code A3-EOT is inputted through the transmission line 6 to the transmission circuits 7, 11, the circuits 7, 11 operate in accordance with the flowchart shown in FIGS. 3 and 4. In other words, the transmission circuit 7 interrupts the data transmission and reception and clears the flags of the transmission. Further, the circuit 7 clears a graph indicating the polling, and selecting status, and identifies whether that station is operated as a transmission station or not. If that station is operated as a transmission station, the circuit 7 resets a transmission data pointer, closed the transmission flag ON, and retransmits as the previous transmission is in error. If that is not operated as a transmission station, the circuit 11 resets the reception data pointer and processes the previous reception as an error and as the previous reception should not be accepted.

The transmission circuit 11 of the light source unit 5 receives the mixed data of the text data and the camera address code, judges it as an transmission error, and delays the reception for a predetermined period of time. When the transmission circuit 11 restarts the receiption, it stores the reception data in the buffer 24. Subsequently, the number m of recognitions (e.g., 3) of the camera address code is set in the counter L (not shown). The circuit 11 judges whether the received data is equal to the previous data or not. If the received data is equal to the previous data, the counter L is counted down. In other words, the circuit 11 judges whether the previous reception data is camera address data or not. If the previous data is not the camera address data, the circuit 11 processes the data as an error. The CPU of the transmission circuit 11 checks whether the received data have been received m times or not. If the received data have not been received m times, the circuit 11 again receives the data. When the received data reach m times, the circuit 11 registers the received data, i.e., the camera address code as the address of the new subscription with the station. Then, whether or not the camera address code is received within the predetermined period of time is judged. If it is YES, an ordinary routine of the control station is performed. If it is NO, the error process routine is performed. When the camera address is registered, the transmission circuit 9 of the camera unit 3 is polled by the transmission circuit 11 of the light source unit 5 together with the circuit 7 of the endoscope unit 1. In the routine of the control station, the CPU of the circuit 11 checks the states of the circuits 7, 9. When the operation of the air feed switch 8 is, for example, detected, an air feed command is fed to the endoscope control circuit 12 of the unit 5, thereby allowing the performing of the air feeding operation. When the operation of the release switch 10 of the camera unit is detected by the CPU of the circuit 11, the CPU of the circuit 11 transmits the photograhing command to the illumination control circuit 13. The circuit 13 permits the photographing light source to emit a light in response to this command or to operate an automatic exposure circuit. At this time, an automatic exposure signal is transmitted and received between the circuits 7, 9 and 11 through the transmission line 6.

According to the present invention as described above, there is provided an endoscope apparatus in which the transmission circuit of the camera unit transmits a self address code for a predetermined number of times when a camera unit is connected newly in the case that the light source unit and the endoscope unit are connected and data are transmitted between both the light source unit and the endoscope unit, the transmission circuit of the light source unit identifies the continuation of the camera unit when receiving the address code for a predetermined number of times, thereby registering the camera address code. Accordingly, the transmission circuit of the light source unit judges the data transmitted from the transmission circuit of the camera unit as an error even if the camera unit is operated, until the address code of the camera unit is registered thereby processing the error. Therefore, no error occurs in the photographing operation.

In the embodiment described above, the numbers n and m of the transmissions and the receptions of the address codes are 8 and 3 times. However, these numbers n and m of the transmissions and the receptions of the address codes depend upon the transmission velocity, data format, the length of the frame, etc., and may be preferably set to n=5 to 100, and m=2 to 5. Further, the self address code of the unit newly mounted may only be A3-EOT and A3, or may be assigned for other characters. In the embodiment described, the unit newly mounted is described as the camera unit. However, other units may also be employed. In the embodiment described above, the transmission circuit of the light source unit is the control station, and the transmission circuit of the other unit is the controlled station. However, either transmission circuit may be the control station. Moreover, the transmission interrupted by the address code of the unit newly mounted may be automatically reset, or may also be arbitrarily selected from the JIS C 6362 (Japanese Industrial Standards) fundamental data transmission controlling sequence and polling/selecting system as the transmission sequence and the synchronization system. In the embodiment described, the self address code of the unit newly mounted is transmitted in response to the mounting of the unit or the turning on of the power source. However, a start switch may be provided, and the self address code may be transmitted by the operation of the start switch.

What is claimed is:

1. An endoscope apparatus comprising:
   an endoscope unit for observation in a body cavity;
   a light source unit connected to said endoscope unit for generating a light illuminating the body cavity through a light guide of said endoscope unit;
   a camera unit connected to an eyepiece section of said endoscope unit for photographing in the body cavity;
   one of said units having first transmission means which becomes a control station unit, and the other of said units each having second transmission means which becomes a controlled station unit, said first transmission means having means for identifying that the controlled station unit is mounted on the control station unit having said first transmission means when said first transmission means receives self address codes, transmitted a first predetermined number of times by at least one of said second transmission means of the controlled station units, a second predetermined number of times from said at least one second transmission means of the controlled station units.

2. The endoscope apparatus according to claim 1, wherein said first transmission means is provided in said light source unit.

3. The endoscope apparatus according to claim 1, wherein said first transmission means comprises means for stopping receiving, for a predetermined period of time, when receiving the self address code of other second transmission means during the communication with one of said second transmission means and means for registering the self address code when receiving the self address codes for a predetermined number of times after the reception is started.

4. The endoscope apparatus according to claim 3, wherein said unit having said second transmission means communicating with said first transmission means is said endoscope unit, and said unit having the other second transmission means is said camera unit.

5. The endoscope apparatus according to claim 1, wherein said first predetermined number of times is 5 to 100 and said second predetermined number of times is 2 to 5.

* * * * *